United States Patent [19]

Purdy

[11] Patent Number: 5,443,478
[45] Date of Patent: Aug. 22, 1995

[54] MULTI-ELEMENT INTRAVASCULAR OCCLUSION DEVICE

[75] Inventor: Phillip D. Purdy, Dallas, Tex.

[73] Assignee: Board of Regents, The University of Texas System, Austin, Tex.

[21] Appl. No.: 939,296

[22] Filed: Sep. 2, 1992

[51] Int. Cl.⁶ ............................................. A61B 17/00
[52] U.S. Cl. ......................................... 606/200; 623/1
[58] Field of Search .............. 606/108, 194, 195, 198, 606/200; 128/899; 623/1, 12

[56] References Cited

U.S. PATENT DOCUMENTS

| | | |
|---|---|---|
| 3,540,431 | 11/1970 | Mobin-Uddin . |
| 3,794,041 | 2/1974 | Frei et al. ............................ 606/108 |
| 3,868,956 | 3/1975 | Alfidi et al. . |
| 4,365,632 | 12/1982 | Kortum . |
| 4,425,908 | 1/1984 | Simon .................................. 606/200 |
| 4,447,227 | 5/1984 | Kotsanis . |
| 4,494,531 | 1/1985 | Gianturco . |
| 4,512,338 | 4/1985 | Balko et al. . |
| 4,619,246 | 10/1986 | Molgaard-Nielson et al. .... 606/200 |
| 4,638,803 | 1/1987 | Rand . |
| 4,957,501 | 9/1990 | Lahille et al. . |
| 4,994,069 | 2/1991 | Ritchart et al. . |
| 4,997,435 | 3/1991 | Demeter . |
| 5,053,008 | 10/1991 | Bajaj . |
| 5,071,407 | 12/1991 | Termin et al. . |
| 5,104,404 | 4/1992 | Wolff ...................................... 623/1 |
| 5,108,407 | 4/1992 | Geremia et al. ..................... 606/108 |
| 5,108,419 | 4/1992 | Reger et al. . |
| 5,256,146 | 10/1993 | Ensminger et al. ................. 606/198 |

Primary Examiner—Stephen C. Pellegrino
Assistant Examiner—William Lewis
Attorney, Agent, or Firm—Arnold, White & Durkee

[57] ABSTRACT

A multi-element occlusion device (10, 20, 30, 40) provides an improvement over existing systems by increasing the occupation of a vascular lumen. The device (10, 20, 30) comprises an anchoring element (12, 22, 32), a lead element (14, 24, 34) and at least one fiber (16, 26, 36) attaching said elements. The elements and fibers produce a cumulative occlusive effect greater than the sum of the individual elements. When placed in the blood stream, the anchoring element (12, 22, 32) lodges against the vessel wall and the lead element (14, 24, 34) is carried to a position distal thereto. With the use of multi-element deployment, the device (10, 20, 30) decreases the risk of continued canalization and recanalization.

7 Claims, 2 Drawing Sheets

MULTI-ELEMENT INTRAVASCULAR OCCLUSION DEVICE

TECHNICAL FIELD OF THE INVENTION

This invention relates to a multi-element intravascular occlusion device for use within blood vessels to decrease the risk of continued canalization and recanalization. Specifically, the device comprises at least one lead element attached to at least one anchoring element.

BACKGROUND OF THE INVENTION

Endovascular use of devices to occlude blood vessels has become widespread both geographically around the world and anatomically throughout the body. In endovascular therapy, the doctor attempts to produce blockage or occlusion of blood flow through a vessel in order to stop bleeding. The vessel may be either an artery or a vein. His goal may be to prevent the vessel from hemorrhaging, to limit bleeding during surgery, or to stop an abnormal blood flow pattern between blood vessels (i.e. fistulas). Devices can also be used to prevent growth of abnormal protrusions from blood vessels, such as aneurysms, by creating an occlusion within the aneurysm. This occlusion minimizes or eliminates the blood pulsations which cause abnormal stresses on the wall of the aneurysm.

Several endovascular devices have been created to accomplish these goals. These devices include "glue," thrombosis producing particles, balloons, and coils. Central to the success of the device is its ability to be precisely placed within the vessel and its ability to adhere to the vessel wall. Placement typically occurs through a catheter from a proximal position outside of a patient to a distal position within the patient. Each type of device has particular advantages and drawbacks in its efficacy and its ability to be placed.

"Glue" refers to a group of compounds that are injected into a vessel. The glue solidifies on the vessel wall. Solidification typically occurs due to exposure of the glue to electrolytes in the blood. Therefore, glue is not actually a "device" which is solid at the time of its introduction. Control of the placement of the glue is hampered due to the variability of its cure rate within the blood stream.

Thrombosis producing particles can also be introduced into the vessel to produce blockage of that vessel. These particles can be formed of various material such as polyvinyl alcohol, silicone polymer, protein particles, glass beads, latex beads, or silk suture material. The blockage may be temporary or permanent, depending on whether and to what degree the particle is broken down in the body, resulting in recanalization of a blood vessel after occlusion. In the case of particles, blockage occurs at the point where the blood vessel diameter is smaller than the particle. Thus, if a small particle is released into a large vessel, the blood flow will carry the particle to the point where the vessel diameter diminishes to that of the particle. This is used to advantage in tumor or vascular malformation embolization, but has the disadvantage of loss of control over the point of occlusion. A balloon can be introduced within the vessel by a catheter and then inflated within the blood vessel to produce occlusion. The balloon may be permanently attached to the catheter, or it can have a valve at the point of attachment which closes when the catheter is withdrawn, detaching the balloon in position without producing subsequent deflation. With balloons permanently attached to a catheter, the blockage generally occurs at the point of placement of the tip of the catheter, such that the level of blockage is limited to the position of the tin of the catheter. That may be far into a vascular system, such as the brain, depending on the flexibility of the catheter and the skill of the operator, but the point of the occlusion is the tip of the catheter.

With detachable balloons, the method of detachment is usually traction of the balloon against the blood vessel, producing friction which causes resistance to withdrawal as the catheter is pulled out. Alternatively, balloons can also be detached by a so-called coaxial detachment system wherein detachment occurs by advancement of a larger catheter over a smaller catheter containing the balloon. The larger catheter contacts the inflated balloon preventing the withdrawal of the balloon. This permits the inner catheter to be removed from the balloon while the balloon maintains its position. However, this system is limited to larger vessels because the stiffness of both the outer and inner catheters limits their ability to advance into ever more tortuous, distal vessel portions.

Balloon occlusion devices can sometimes deflate or can even rupture the artery in which they are introduced, thus being somewhat hazardous and unpredictable. Also, balloon devices limit embolization options by producing vascular occlusion at the time of introduction. Thus, if combined embolization is desired using both particles and a more proximal occlusive device such as a balloon, the use of the balloon precludes the first use of the particles. Thus, balloons have the advantage of control over the point of occlusion but the inability to perform combined embolization while particles have the disadvantage of a lack of control over the point of occlusion.

A more recent endovascular device for small vessels, "coils," have been used for many years to present a solution to these problems in larger vessels. A coil is typically a stainless steel wire device wound such that its outer diameter matches the inner diameter of an angiographic catheter. The coil can be introduced into a catheter in a straight configuration and pushed through the catheter with a guide wire. As it exits the catheter, it can wind itself into a "coil" type configuration. The coil produces an obstacle in the blood vessel, causing blood to clot thereon. The clot blocks the blood vessel. Further development resulted in the addition of fibers of cotton or other material within the coil, increasing its propensity to cause thrombosis more quickly.

In recent years, advancements in catheter technology have allowed progressively more distal catheterizations. However, with more distal catheterizations, the stiffness of the stainless steel coil is a limitation. In response, small-diameter platinum "microcoils" were developed. These microcoils can be introduced through the catheter with a guide wire or, alternatively, be pushed by the force of an injection of water through the catheter, thus "injecting" them into the blood vessel. Some of these "coils" are actually straight, thus enabling them to follow flow in the vessel and act more like a particle. Some are curved, thus increasing the likelihood that they will not advance beyond the point of introduction. Still, all traditional coils have the disadvantage of a lack of control, insofar as they are free objects once they are introduced into the catheter. If the coils leave the catheter tip flowing in an untoward direction or if the catheter tip moves at the time of introduction, the physician has no control over this undesirable situation or ability to recall or reposition the coil. Thus, their successful placement is extremely dependent on the skills of the surgeon/radiologist placing them.

Additionally, coils often fail to produce complete occlusion of the vessel. Because of continued canalization or recanalization, blood flow through the partially occluded vessel continues. Also, because of the size of the coils, complete occlusion of the vessel often requires that multiple coils be placed to ensure occlusion. The additional coils add expense and lengthen the time necessary to complete the procedure.

Therefore, a need exists for a more widely applicable intravascular occlusion device. Such an occlusion device should produce the greatest amount of occlusion with the most flexible device. The occlusion device can even be a hybrid combination of other such devices. Given the time and expense involved in using intravascular coils, this new device should save substantial time and money via the use of fewer units to achieve the desired end.

SUMMARY OF THE INVENTION

The present invention relates to a multi-element intravascular occlusion device comprising at least one lead element attached to at least one anchoring element by at least one fiber. The lead element can be either a particle or a coil. Likewise, the anchoring element can be either a particle or a coil. Interference of flow created by the fiber linking the elements will exceed the sum of the effect of the separate elements. Instead of clotting on a single particle or coil, the blood clots around each part of the device. The resulting occlusion is deeper and thus decreases the risk of continued canalization or recanalization.

The present invention will also save time and money. Instead of requiring the placement of several coils or particles to achieve occlusion, the device allows a more rapid occlusion with fewer deployments. The device can be placed into a vessel by conventional means to create thrombosis and thereby occlude continued blood flow.

Either the lead element or anchoring element can be made of almost any material and can be almost any shape. For example, current occlusive particles include glass beads and protein particles to produce occlusion. The particles come in several different sizes and shapes. A coil can be made of stainless steel, platinum, or other suitable material. Like the particles, the coils are also available in varying shapes and sizes. The most desirable material, shape and size for the device will depend on the individual circumstances of the desired occlusion. Typically, the size will be limited by the catheter used to place the occlusion device.

Once the occlusion device exits the catheter, the device can flow downstream until the anchoring element lodges against the vessel wall. Typically, the anchoring element will lodge at that point where its circumference is greater than that of the vessel wall. In an alternate embodiment, the anchoring element can have forward prongs which penetrate the vessel wall, thereby fixing the position of the anchoring element. The lead element flows to a position distal to the anchoring element. Thus, the lead element will usually be somewhat smaller than the anchoring element.

The lead element is connected to the anchoring element by at least one fiber. The fiber can be either metallic or nonmetallic. It can be attached to the lead and anchoring elements chemically or mechanically. The length of the at least one fiber can determine the distance the lead element can flow downstream from the anchoring element. In a preferred embodiment, several fibers are used. The fibers can be of the same or different lengths. Likewise, the stiffness of the fiber can be controlled to limit the positioning of the lead element. For example, a doctor may use a device with flexible synthetic fibers if the location of the desired occlusion is in a blood vessel which has sharp turns. In other cases, several stiff fibers made of steel may be needed to prevent the lead element from moving. In some cases, the circumstances may even require a fiber capable of elongation.

In an alternate embodiment, a single anchoring element is used with several lead elements. The lead elements can be arranged sequentially, or can be attached to the anchoring element as separate branches. In fact, one embodiment could comprise a single anchoring dement with two branches extending therefrom, wherein one branch comprises a single lead element while the other branch comprises several lead elements attached sequentially. In another embodiment, two or more anchoring elements might be used with a single lead element. In another embodiment, several fibers can be intertwined to create a lead element.

BRIEF DESCRIPTION OF THE DRAWINGS

For a more complete understanding of the present invention, and for further details and advantages thereof, reference is now made to the following Detailed Description taken in conjunction with the accompanying drawings, in which.

DETAILED DESCRIPTION OF THE INVENTION

Figure 1:
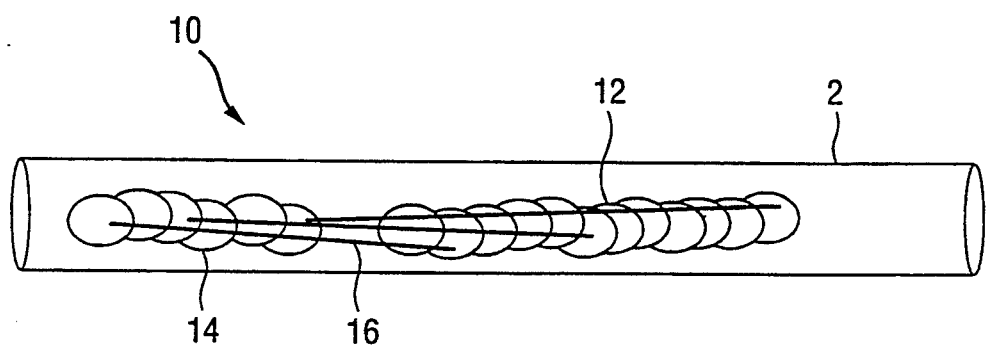
FIG. 1 provides a perspective view of the device compressed within an introducing catheter.
Figure 2:
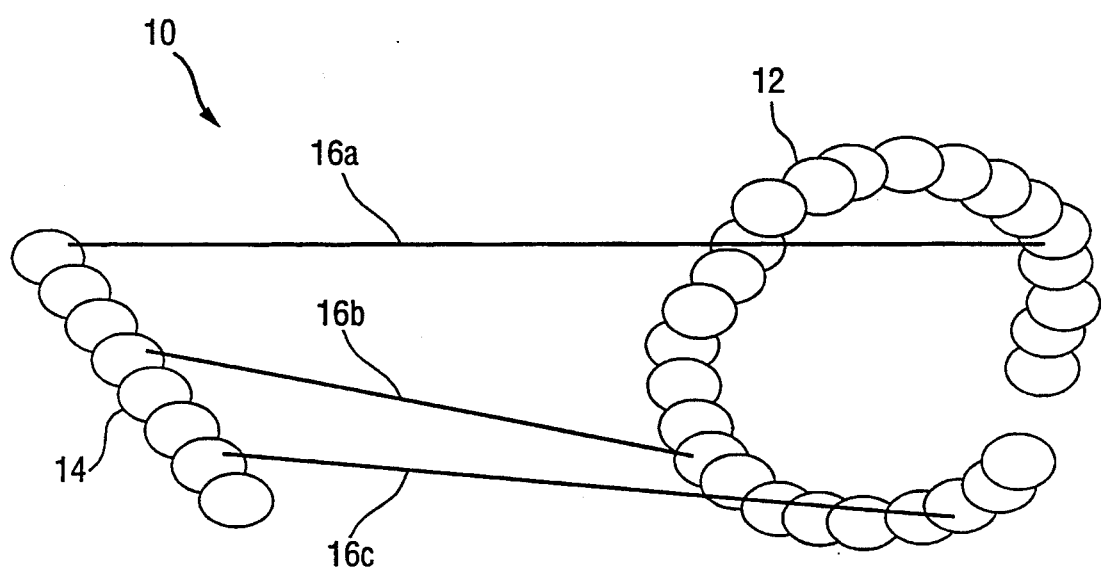
FIG. 2 shows a perspective view of a first embodiment deployed wherein the lead dement is a coil.

The present invention relates to a multi-element intravascular occlusion device which overcomes many of the disadvantages in the prior art. FIGS. 1 and 2 illustrate a first embodiment of the device 10 in both a compressed and a deployed configuration. The device 10 comprises an anchoring element 12 and a lead element 14 connected by fibers 16, wherein both elements are coils. An introducing catheter 2 is used to place the device 10 into a blood vessel. As the device 10 is placed in the vessel, the anchoring element 12 deploys and lodges against the wall of the vessel. The blood flow carries the lead element 14 distally up to the length of the fibers 16. Blood clots form around the anchoring element 12, the fibers 16 and the lead element 14 to occlude blood flow through the vessel.

The potential shape of the coils are unlimited. Currently, numerous configurations of coils exist. For example, a "Gianturco coil" by Cook, Inc. includes multiple turns into a spring-like shape. Another coil, the Flower coil by Target Therapeutics, includes multiple turns which are offset from one another. Hilal coils, also manufactured by Cook, Inc., include either single turns or straight configurations of various lengths or diameters. It is anticipated, however, that the initial configuration of the device 10 will contain a curved anchoring element 12, as shown.

Though the size of the lead element 14 will vary, it will generally be smaller than that of the anchoring element 12. The smaller the size of the lead element 14 relative to the anchoring element 12, the more likely it is that the lead element will be carried distally by the blood flow. Unlike the curved anchoring element 12, the lead element 14 in the anticipated initial configuration of the device 10 will comprise a straight coil as shown.

A plurality of fibers 16a, 16b, 16c serve as a means for connecting the anchoring element 12 and the lead element 14. Fibers 16 are typically between 3 and 30 mm in length. However, they may be any length suitable for the application. Moreover, the fiber 16 may be capable of elongation. The material used for the fiber 16 can affect the behavior of the lead dement 14. For some uses, the fibers 16 should be made of metal. In other applications nonmetallic fibers 16 are preferable. The desired behavior of the device 10 and factors such as strength, flexibility, or bonding to the other elements will determine the material used.

The attachment of the fibers 16a, 16b, 16c to the anchoring element 12 and the lead element 14 may be achieved by solid or mechanical means. Solid attachment may be achieved by use of solder or glue materials or by melding or fusion of the two. Mechanical attachment may be achieved by tying or twisting a fiber 16 onto the other elements. The attachment of the elements will be a function, to some extent, of the desired application.

Figure 3:
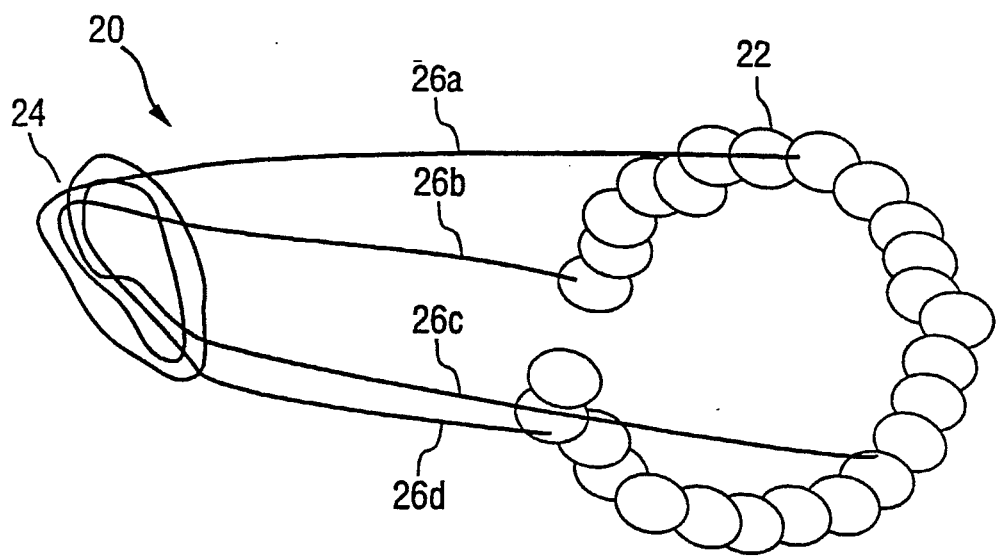
FIG. 3 gives a perspective view of a second embodiment wherein the lead dement is comprised of intermeshing fibers.

FIG. 3 illustrates occlusion device 20 which represents a second embodiment of the present invention. The occlusion device 20 comprises an anchoring element 22 and a lead element 24 connected by fibers 26a, 26b, 26c, 26d. The anchoring element 22 comprises a coil similar to that shown in FIG. 2. The lead element 24, however, is formed by an intermeshing of fibers 26. The distance between the lead element 24 and the anchoring element 22 can be controlled both by the length of the fibers 26 and the location at which the fibers are intermeshed. The fibers 26 may be held together by a knot, or by some other means such as glue.

The lead element 24, as illustrated, acts like a thrombosis producing particle. Therefore, the lead element 24 can be any other thrombosis producing particle such as polyvinyl alcohol, silicone polymer, protein particles, glass beads, latex beads, or silk suture material.

Figure 4:
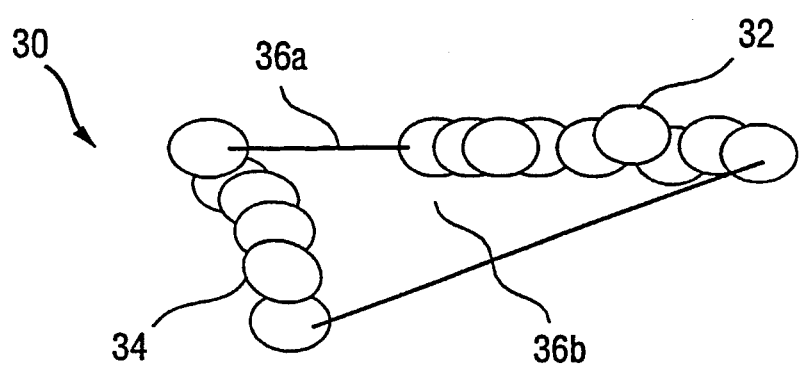
FIG. 4 provides a perspective view of a third embodiment in which the lead dement and the anchoring elements are attached by fibers with different lengths.
Figure 5:
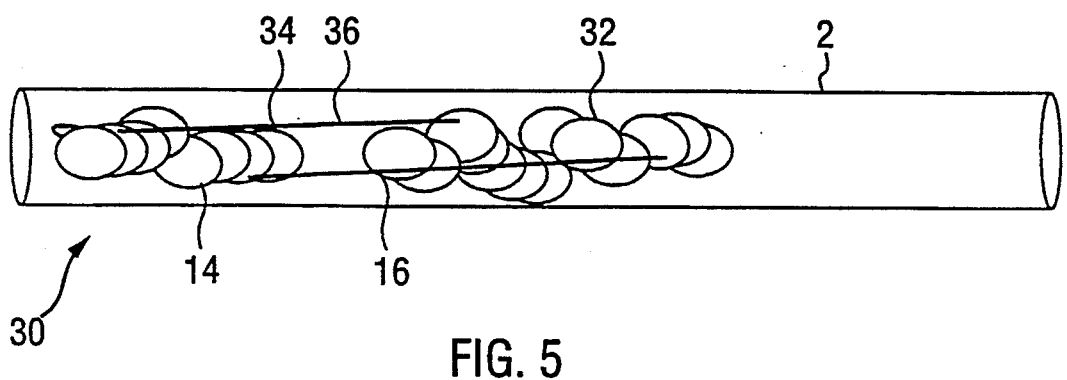
FIG. 5 illustrates a perspective view the device in FIG. 4 contained within an introducing catheter.

FIGS. 4 and 5 illustrate occlusion device 30 which represents a third embodiment of the present invention. Again, the occlusion device 30 comprises an anchoring element 32 and a lead element 34 connected by two fibers 36a, 36b. Both the lead and anchoring elements 32, 34, are shown as straight coils. As shown, fiber 36a is shorter than fiber 36b. Both fibers can be attached to any part of either element. Fibers 36a and 36b are attached to opposite ends of each coil. By varying the numbers of fibers 36 and where they attach the other elements, the behavior of the lead element 34 can be altered.

The mechanism of delivery for device 10, 20, 30 can incorporate any of the currently available mechanisms. These include either mechanical pushing of the coil through the introducing catheter 2 by a guide wire, injection of the coil using saline or other liquid to wash it from the introducing catheter 2, or use of a detachment apparatus which allows for controlled delivery or withdrawal. Utilization of the system will most frequently occur via a transfemoral catheterization, either arterial or venous. An angiographic catheter will be placed such that its tip is near the desired deployment location. In some cases, this will involve a coaxial catheterization. For instance, in cerebral embolizations it is common to place an catheter from the femoral approach into the carotid or vertebral artery. From there, a second smaller catheter is inserted by way of the angiographic catheter and advanced to a point within the brain near the pathology, and the embolization is conducted through this smaller catheter. In these situations, that smaller catheter becomes the introducing catheter 2 for purposes of this application, since it is the most distally placed catheter through which the device will be introduced.

Following angiographic verification of placement of the introducing catheter 2, the device will be introduced into the hub of the introducer. Following introduction, the device is advanced until it can be seen under fluoroscopy that it is exiting the introducing catheter 2. With a free-standing coil, the device's exit from the introducing catheter 2 will result in final placement. With a detachable device, the detachment is performed when the device is observed to have exited the introducing catheter 2 completely and is in an appropriate position and configuration. Since the detachment of the device and subsequent removal of the detaching system do not require removal of the introducing catheter 2, the same process may be repeated if additional devices are required.

A multi-element occlusion device may be more difficult to retract. Since the lead dement 14, 24, 34 can already be free of the introducing catheter 2, it may become caught at the time of attempted retraction. Variations in design may be used in situations wherein detachable devices are used or in which a potential need for retraction may be anticipated. Though devices now exist which are designed for coil retrieval after placement, it is anticipated that deposition of this device into the vascular space is permanent. The intent is to induce permanent occlusion of a blood vessel or cavity or permanent obliteration of a space.

Although preferred embodiments of the invention have been described in the foregoing Detailed Description and illustrated in the accompanying drawings, it will be understood that the invention is not limited to the embodiments disclosed, but is capable of numerous rearrangements, modifications, and substitutions of parts and elements without departing from the spirit of the invention. Accordingly, the present invention is intended to encompass such rearrangements, modifications, and substitutions of pans and elements as fall within the scope of the invention.

I claim:

1. A multi-element intravascular occlusion device comprising:
   (a) at least one anchoring means for anchoring the device to a wall of a vessel; and
   (b) at least one lead element for travelling distal to the anchoring means and producing thrombosis within the vessel, said lead element being attached to said at least one anchoring means by a means for attaching, wherein said anchoring means comprises a coil, and wherein in use, the device is free-standing within the vessel, and blood in the vessel clots on the anchoring means, the lead element, and the attaching means to produce total occlusion of the vessel.

2. The multi-element intravascular occlusion device of claim 1, wherein the coil is curved.

3. The multi-element intravascular occlusion device of claim 1, wherein the coil is straight.

4. A multi-element intravascular occlusion device comprising:
   (a) at least one anchoring means for anchoring the device to a wall of a vessel; and
   (b) at least one lead element for travelling distal to the anchoring means and producing thrombosis within the vessel, said lead element being attached to said at least one anchoring means by a means for attaching, wherein said means for attaching comprises at least one fiber, and wherein said at least one fiber comprises a fiber capable of elongation.

5. A multi-element intravascular occlusion device comprising:
   (a) an anchoring means for anchoring the device to a vessel wall;
   (b) a lead element for travelling distal to the anchoring means; and
   (c) a plurality of fibers for attaching said anchoring means to said lead element, wherein said lead element comprises a particle means for producing thrombosis.

6. A multi-element intravascular occlusion device comprising:
   (a) an anchoring means for anchoring the device to a wall of a vessel;
   (b) a lead element for travelling distal to the anchoring means and producing thrombosis within the vessel; and
   (c) a plurality of fibers for attaching said anchoring means to said lead element, wherein said plurality of fibers comprise nonmetallic fibers.

7. A method of producing total occlusion of a vessel using a multi-element intravascular occlusion device at a desired deployment location, said device having at least one anchoring element and at least one lead element attached by at least one fiber, said method comprising:
   (a) inserting an introducing catheter with a distal end into the vessel such that the distal end is adjacent to the desired deployment location;
   (b) inserting the occlusion device into the introducing catheter;
   (c) introducing the occlusion device into the vessel from the introducing catheter;
   (d) lodging the anchoring element against the vessel wall; and
   (e) allowing the lead element to travel distal to the anchoring element, said lead element producing thrombosis within said vessel.

* * * * *